United States Patent
Heczko et al.

(10) Patent No.: US 8,632,766 B2
(45) Date of Patent: Jan. 21, 2014

(54) **STRAIN COMPOSITION OF THE *LACTOBACILLUS* GENUS AND THE APPLICATION OF STRAIN COMPOSITION OF THE *LACTOBACILLUS* GENUS**

(75) Inventors: Piotr B. Heczko, Krakow (PL); Magdalena Strus, Krakow (PL); Grzegorz Stefański, Warszawa (PL); Katarzyna Dechnik, Krakow (PL)

(73) Assignee: Instytut Biotechnologii Surowic I Szczepionek Biomed S.A., Krakow (PL)

( * ) Notice: Subject to any disclaimer, the term of this patent is extended or adjusted under 35 U.S.C. 154(b) by 1203 days.

(21) Appl. No.: 12/156,780

(22) Filed: Jun. 4, 2008

(65) Prior Publication Data
US 2008/0299099 A1    Dec. 4, 2008

(30) Foreign Application Priority Data
Jun. 4, 2007    (PL) .......................................... 382579

(51) Int. Cl.
*A01N 63/00* (2006.01)
*C12N 1/20* (2006.01)

(52) U.S. Cl.
USPC .................. 424/93.45; 435/252.4; 435/252.9; 435/853; 435/857

(58) Field of Classification Search
None
See application file for complete search history.

(56) References Cited

U.S. PATENT DOCUMENTS

2005/0244392 A1    11/2005    Pei et al.
2006/0062773 A1*    3/2006    Davis et al. ................ 424/93.45

FOREIGN PATENT DOCUMENTS

| ES | 0994183 | 4/2000 |
|---|---|---|
| PL | 184037 | 2/1998 |
| PL | 189577 | 11/1999 |
| PL | 190233 | 12/1999 |
| WO | 2006038869 | 4/2006 |
| WO | 2007040444 | 4/2007 |

OTHER PUBLICATIONS

"Potential Role of Natural Antioxidants in the Prevention of Some Human Diseases" 4th Priobiotics Prebiotics New Foods Meeting, Sep. 2007, pp. 1-13.
Functional Food Preparation: Evidence Based Claims on Functionality, Technological Issues, Safety and Efficacy, 4th Probiotics Prebiotics New Foods Meeting, Sep. 2007, pp. 1-13.
"The Influence of Oral Administration of Three Pro-biotic *Lactobacillus* Strains on the Enhancement of the pH and Composition of the Vaginal Micro Floral in Women of Reproductive Age"— Ginekologia to Dyplomitz—Mar. 2008.

* cited by examiner

*Primary Examiner* — Debbie K Ware
(74) *Attorney, Agent, or Firm* — Horst M. Kasper

(57) ABSTRACT

A subject of the invention is a composition containing strains *Lactobacillus fermentum* 57A, *Lactobacillus plantarum* 57B and *Lactobacillus gasseri* 57C of special characteristics such as a feature of strong diversified affinity for the digestive tract and vaginal epithelia enabling the colonization of the vagina and anus after the crossover through intestines as well as the feature of co-aggregation enabling for synergetic activity. The subject of the invention is also the application of the composition for restoration of the natural bacterial flora of the vagina and anus.

4 Claims, 2 Drawing Sheets
(2 of 2 Drawing Sheet(s) Filed in Color)

1. Positive control - *Lactobacillus plantarum* 14431 ATC
2. *Lactobacillus plantarum* 57B
3. Negative control
4. DNA isolated from a co-aggregate (as shown in Fig.1).
5. Marker 1. Positive control - *Lactobacillus fermentum* DSM 20052
2. *Lactobacillus fermentum* 57A
3. DNA isolated from a co-aggregate (as shown in Fig. 1)
4. Negative control
5. Marker

STRAIN COMPOSITION OF THE *LACTOBACILLUS* GENUS AND THE APPLICATION OF STRAIN COMPOSITION OF THE *LACTOBACILLUS* GENUS

BACKGROUND OF THE INVENTION

1. Field of the Invention

The subject of the invention is the strain composition of the *Lactobacillus* genus and the application of the strain composition of the *Lactobacillus* genus in the production of the pharmaceutical preparation.

2. Brief Description of the Background of the Invention Including Prior Art

The composition of the vaginal microflora is diverse and depends on the stage of life a woman is in and is strictly dependent on hormonal activity of the body. Basic knowledge of the vaginal ecosystem was put forward by Cruickshank and Sherman, who described the vaginal microflora of the fetus in the uterus, of infants, girls before puberty, and women in the reproductive phase and after menopause. In the uterus the fetal vagina is sterile, however, 2-3 weeks after birth the quantitative composition of microflora is almost the same as the quantitative composition of microflora of an adult woman's vagina, which is the consequence of estrogen stimulation by the mother. Before the occurrence of the first menstruation, vaginal environment is dominated by bacteria such as *S. epidermidis, Bacteroides* spp., *Peptococcus* spp., *Porphyromonas* spp., *G. vaginalis*. During the reproductive period the vaginal environment is mostly dominated by bacterial population of the *Lactobacillus* genus. In the past it was believed that this genus is represented by one strain only, that is *Lactobacillus acidophilus*. During the last decade the development of modern molecular methods allowed to sort out the classification of most of the bacteria, which proved that the *Lactobacillus acidophilus* species is not homogenous and is a part of a complex of a few other species such as *L. crispatus, L. amylovorus, L. gallinarum, L. acidophilus sensu stricto, L. gasseri, L. johnsoni*. Using modern molecular methods, especially the DNA sequencing technique, as well as modified culturing procedure it was proven that the most common strains found in the natural vaginal environment of healthy women are some various species, which are a part of the acidophilus complex such as *L. johnsoni, L. gasseri, L. acidophilis, L. crispatus*, and above all *L. plantarum* and *L. fermentum*.

The mechanisms by which the bacteria from the genus *Lactobacillus* effect the vaginal environment are not yet fully understood. However, it is widely known that they:
- synthesize antimicrobial substances, such as lactic, acetic, pyroglutamic acids, in order to lower the pH of the vaginal environment to obtain the values of 3.7-4.6,
- synthesize short peptides and/or proteins with a very complex structure, resembling bacteriocins, which adhere to the receptors at the surface of susceptible bacteria leading to their lyses and eventually their death,
- compete with other microorganisms, especially pathogenic, for nutritive substances and for the epithelial receptors of the vagina,
- modify toxins and toxins' receptors,
- produce hydrogen peroxide—some *Lactobacillus* strains, which produce $H_2O_2$, dominate the microbe population of healthy vagina,
- exert different immuno-modulating effects on the host's immunological system.

Due to these many different properties, the bacteria of the *Lactobacillus* genus are able to maintain a certain biological state of equilibrium of the vagina, preventing the numerous population growth of pathogenic microorganisms residing in the woman's genital tract, which also decreases the risk of occurrence of bacterial vaginosis.

Due to the fact that most of infections of the genitourinary tract in women are caused by the imbalance of the vaginal microflora, the ways of prevention as well as treatment are directed towards restoration of correct microbial balance.

In 1992, in the United States an experiment was carried out (Hilton E, Isenberg H D, Alperstein P, France K, Borenstein M T. Ingesting of yogurt containing *Lactobacillus acidophilus* as prophylaxis for candidal vaginitis. Ann Item. Med 1992; 116: 353-357), which involved a consumption of yogurt containing *Lactobacillus acidophilus* on daily basis for 6 months by 35 women with recurring candidiasis of vulva and vagina in order to prevent the recurring illness. The endpoint of the experiment was colonization of vagina and anus by *Candida* and *Lactobacillus* as well as candidiasis. Thirteen patients finished the experiment, however, the analysis was done for 33 of them. During the 6-month period a relevant decrease in the number of infections caused by *Candida* was found in persons who were colonized (anus and vagina) by *Candida*. An experiment was done with the use of a regular yogurt containing *L. acidophilus*, which produced a moderate quantity of $H_2O_2$. The strains of *L. acidophilus* isolated from the women were not identified. However, a close relationship between the presence of *L. acidophilus* in the anus and vagina was observed: if *L. acidophilus* was absent in the anus, the probability of its presence in the vagina was 15.5%, on the other hand, if present in the anus, the probability of its presence in the vagina was 54.8% (P<0.001). The authors concluded that the intestinal strain of *L. acidophilus* was colonizing the vagina, however, due to the lack of molecular evidence, it was impossible to prove.

A similar experiment was done in 1996 in Israel (Shalev E, Battino S, Weiner E, Colodner R, Keness Y. Ingestion of yogurt containing *Lactobacillus acidophilus* compared with pasteurized yogurt as prophylaxis for recurrent candidal vaginitis and bacterial vaginosis. Arch Fam Med 1996; 5: 593-596) based on the same protocol and with the use of yogurt containing *L. acidophilus* producing $H_2O_2$. The data obtained in this experiment did not show a prophylactic activity on the recurrent vaginal blastomycosis (the same effect was shown by the yogurt containing dead bacteria), however, it showed an effect on bacterial vaginosis, at the same time increasing the number of women colonized by *L. acidophilus*. Also, a coexisting colonization of the anus and vagina by *Candida* was observed.

In 2001, in Finland (Kontiokari T, Sundqvist K, Nuutinen M, Pokka T, Koskela M, Uhari M. Randomized trial of cranberry-lingonberry juice and *Lactobacillus* GG drink for the prevention of urinary tract infections in women. Brit Med J 2001; 322: 1571-1573) an open randomized experiment on the possibility of preventing recurring urinary tract infections in women was carried out with the use of cranberry and lingonberry juice or *Lactobacillus* GG drink. The experiment lasted for 12 months and involved the observation of recurring infections in 150 women divided into 3 groups, who were earlier diagnosed with an urinary tract infection (>$10^5$ bacteria/ml of urine). The final parameter of the experiment was the observation of a recurring infection. As compared to the cranberry/lingonberry juice, a positive effect of *Lactobacillus* GG was not observed. The cause of this may be that *Lactobacillus* GG, being a typical intestinal strain, does not colonize the urethra opening/vagina.

In 2003 (Reid G, Charbonneau D, Erb J, Kochanowski B, Beuerman D, Poehner R, Bruce A W. Oral use of *Lactobacil-*

*lus rhamnosus* GR-1 and *L. fermentum* RC-14 significantly alters vaginal flora: randomized, placebo-controlled trail in 64 healthy women. FEMS Immunol Med Microbiol 2003; 35: 131-134) a randomized clinical experiment with the use of placebo was carried out in order to check the effect of *Lactobacillus rhamnosus* GR-1 and *L. fermentum* RC-14 orally administered for 60 days on vaginal flora of 64 healthy women. Microscopic analysis showed that 37% of the examined women returned to their normal flora compared to the 13% of women from the control group. The culture showed a relevant increase in the number of *Lactobacillus*, and a decrease in the number of yeasts and intestinal rods. The probiotic was considered safe upon daily administration.

In 2004, the same authors carried out another experiment where the same strains (Reid G, Burton J, Hammond J A, Bruce A W. Nucleic acid-based diagnosis of bacterial vaginosis and improved management using probiotic lactobacilli. J Med Food 2004; 7: 223-228) were administered to 59 women with non-symptomatic bacterial vaginosis diagnosed with the help of DGGE. After 2 months of probiotic administration, the restoration of the microbial flora of the vagina, dominated by *Lactobacillus*, was shown.

Migration (cross-colonization) of bacteria from the anus to vagina also involves pathogens such as: *Streptococcus agalactiae*, uropathogenic strains of *Escherichia coli* or *Staphylococcus aureus*. In the recently published paper (Warner J E, Onderdonk A B. Diversity of toxic shock syndrome toxin I-positive *Staphylococcus aureus* isolates. Appl Environ Microbiol 2004; 70: 6931-6935) it was shown, with the use of the PFGE method, that the same strains of *S. aureus* are present in both places in 59% of examined women.

It should be noted that there is a lack of proof in literature for migration or cross-colonization of the anus and vagina by the same strains of *Lactobacillus*. This may be due to the fact that in the past the adequate molecular typing methods were not known. Additionally, the administration of the *Lactobacillus* strains with dairy products is not possible in all the patients due to dietary reasons. The described *Lactobacillus* strains, administered orally, showed inadequate survival in the digestive tract and required protection of special capsules.

It is known from the Polish patent's description no. 189577, the use of pairing between lactic acid bacteria of the strain *Lactobacillus brevis* and *Lactobacillus salivarius* subspecies *salicinius* for production of pharmaceutical composition used for vaginal administration in order to treat vaginosis and vaginal infections. The addressed patent's description also reveals the pharmaceutical composition containing the paired lactic acid bacteria of the strains *Lactobacillus brevis* and *Lactobacillus salivarius* subspecies *salicinius*. Based on the obtained data (Strus M., The basics in using probiotics administered into the vagina during the infections of genitourinary tract. Infections, 2005, 4, 40-43) it is concluded that vaginal microflora of healthy women is mainly composed of a few strains of *Lactobacillus*. It was shown that the strains isolated most often were the strains of the *L. acidophilus* complex, as well as the strains: *L. fermentum* and *L. plantarum*. The strains used, based on the patent's description no. 189577, were not characteristic for the Polish women population. Additionally, the form of administration (vaginal) is uncomfortable for daily use.

There are new strains known from the Polish patent's description no. P-373518: *Lactobacillus fermentum* 57A deposited under number-B/00007, *Lactobacillus plantarum* 57B deposited under number-B/00008, *Lactobacillus gasseri* 57C deposited under number-B/00009, *Lactobacillus plantarum* 78B deposited under number-B/00010.

The subject of the invention is also the composition of new strains of the genus *Lactobacillus*, which includes strains *Lactobacillus fermentum* 57A, *Lactobacillus plantarum* 57B, *Lactobacillus gasseri* 57C, with relative numbers in the proportion of 0.5:0.5:1.

The above-said strains were obtained from the posterior vaginal vault of a healthy woman who had a normal vaginal flora. The performed tests showed that the strains *Lactobacillus plantarum* 57B, *Lactobacillus fermentum* 57A, *Lactobacillus gasseri* 57C comply with all the requirements laid down to probiotic products. Based on the performed tests it may be concluded that the new strains are more favorable in comparison to the other tested strains. In addition, each one of the selected and deposited strains possesses a strong leading characteristic. The strain *Lactobacillus plantarum* 57B is characteristic for strong antagonistic features especially for pathogens such as: *Gardnerella vaginalis* and *Escherichia coli*, *Lactobacillus fermentum* 57A adheres very well to the epithelium of the host, and *Lactobacillus gasseri* 57C produces large amounts of hydrogen peroxide.

SUMMARY OF THE INVENTION

1. Purposes of the Invention

The aim of the invention is the development of a strain composition from the genus *Lactobacillus* which could be used to effectively restore the right bacterial flora of the vagina by administering it in the most comfortable form.

2. Brief Description of the Invention

The essence of the invention is a composition containing strains from the genus *Lactobacillus* and its use. The composition containing strains *Lactobacillus fermentum* 57A, *Lactobacillus plantarum* 57B and *Lactobacillus gasseri* 57C possesses special characteristics showing strongly diversified nature in the field of affinity to the epithelium of the digestive tract and vagina which enables the colonization of vagina and anus after migration through intestines, and the co-aggregation characteristics enabling a synergetic effect of each component. The composition can bind with any pharmaceutically compatible carriers and/or supplementary substances. The composition is administered orally, in the form of a capsule.

Application of a composition of new strains of the *Lactobacillus* genus, containing *Lactobacillus fermentum* 57A, *Lactobacillus plantarum* 57B and *Lactobacillus gasseri* 57C of special characteristics such as: diversified affinity for digestive tract and vaginal epithelia enabling the colonization of the vagina and anus orifice after the crossing through intestines, and its ability of co-aggregation enabling synergetic action, for production of pharmaceutical preparation for oral administration in order to restore the natural bacterial flora of the vagina and anus.

Application of the composition consists in preparation of a portion of the pharmaceutical preparation composed of lyophilized strains of bacteria *Lactobacillus fermentum* 57A, *Lactobacillus plantarum* 57B and *Lactobacillus gasseri* 57C and a pharmaceutically compatible carrier and/or supplementary substances, enclosed in a capsule.

Surprisingly, it was found that the strain composition from *Lactobacillus* genus possesses a unique ability to simultaneously colonize vagina and anus. The used strains of *Lactobacillus* genus are not influenced by the conditions typical for digestive tract, thus, the composition is predestined for oral administration.

Surprisingly, it was concluded that the strains of *Lactobacillus* genus of the composition possess a unique characteristic of mutual co-aggregation.

The strain *Lactobacillus fermentum* 57A has a very good affinity for the intestinal epithelium and possesses the ability to adhere to that epithelium, and thus, is able to create conditions for its colonization. Because the strain *Lactobacillus gasseri* 57C has a very good affinity for vaginal epithelium and does not possess that strong of an affinity for the intestinal epithelium, it would not be able to colonize such surface on its own. The phenomenon of co-aggregation with other strains also allows, indirectly, to take part in the colonization of intestinal epithelium, and thus, the anus. In this manner, numerous *Lactobacillus gasseri* populations arise in the digestive tract, which have greater chance for crossing to the vaginal epithelium, which is a natural habitat for this genus, and to which they show a high degree of affinity. Thus, such facilitated crossing over by *Lactobacillus gasseri* 57C and the other two strains to the vaginal ecosystem due to co-aggregation causes a fast colonization of vaginal epithelium.

I. STUDY OF RESISTANCE OF THE COMPOSITION CONTAINING *LACTOBACILLUS* STRAINS ON THE CONDITIONS PRESENT IN THE DIGESTIVE TRACT

1. Survival of the *Lactobacillus* Strains in Low pH Corresponding to the pH of Gastric Juice.

Survival of the *Lactobacillus* strains in low pH was shown based on the modified Lankaputra and Shah method (1995). The studied *Lactobacillus fermentum* 57A, *Lactobacillus plantarum* 57B and *Lactobacillus gasseri* 57C were grown in liquid MRS medium. The culture was grown in anaerobic conditions at 37° C. for 24 hours. After that time, using the method of multiple dilutions, density of each of the strains was determined. Next, with the use of 1N HCl, pH of culture medium was lowered to the value of 1.2, which is equal to the pH of gastric juice. Furthermore, the cultures were incubated for 20 minutes under anaerobic conditions at 37° C., and then they were inoculated in order to determine the degree of reduction in studied bacterial populations due to low pH conditions. The results are shown in Table 1.

TABLE 1

Resistance of *Lactobacillus* strains on low pH.

| | Bacterial density in c.f.u./1 ml | |
| --- | --- | --- |
| Strain tested | Initial density | Density after 20 min. incubation |
| *L. fermentum* 57A | $2 \times 10^8$ | $1 \times 10^6$ |
| *L. plantarum* 57B | $1 \times 10^9$ | $2.2 \times 10^7$ |
| *L. gasseri* 57C | $2.5 \times 10^8$ | $3 \times 10^6$ |
| Control-*L. rhamnosus* GG | $1 \times 10^8$ | $1 \times 10^7$ |

2. Survival of *Lactobacillus* Strains in Artificial Gastric Juice.

Survival of the *Lactobacillus* strains in artificial gastric juice was shown based on the modified Pederson and et. al. method (2004). The studied strains of *Lactobacillus fermentum* 57A, *Lactobacillus plantarum* 57B and *Lactobacillus gasseri* 57C were grown in the liquid MRS medium. The culture was carried out in anaerobic conditions at 37° C. for 24 hours. Next, 100 μl of each strain culture with the density of about $10^8$-$10^9$ c.f.u./1 ml were transferred to 10 ml of the artificial gastric juice (7 ml of 36% HCl, 3.6 g of pepsin [Difco], 2 g of NaCl per 1 l distilled water) with the pH of 2.5 established with the use of 1N HCl. Initial density of each of the bacterial strains was determined by applying the serial dilution method. Next, the cultures were incubated for 20 minutes under anaerobic conditions at 37° C. after which the strains were inoculated in consecutive dilutions in order to determine the degree of reduction of the tested bacterial populations due to the nature of the artificial gastric juice.

The results are shown in Table 2.

TABLE 2

Survival of the *Lactobacillus* strains in artificial gastric juice with pepsin.

| | Bacterial density in j.t.k./1 ml | |
| --- | --- | --- |
| Strain tested | Initial time | After 20 min. incubation period in artificial gastric juice of pH 2.5 |
| *L. fermentum* 57A | $1.3 \times 10^7$ | $8 \times 10^5$ |
| *L. plantarum* 57B | $1.4 \times 10^7$ | $29.1 \times 10^8$ |
| *L. gasseri* 57C | $2 \times 10^6$ | $9 \times 10^5$ |
| Control-*L. rhamnosus* GG | $6.9 \times 10^7$ | $2.5 \times 10^7$ |

3. Resistance Determination of the *Lactobacillus* Strains on Bile Salts.

To determine the resistance of the tested *Lactobacillus* strains on bile salts the Dashkiewicz and Feighner's method was used (1989). This method employs the addition of indicative dye-crimson bromocresol [POCH] in the amount of 0.17 g/l as well as bile salts [OXGAL Difco's company] in the following concentrations: 1 g/l, 2 g/l, 5 g/l, 10 g/l, 20 g/l. Permanent MRS medium/base/prepared in this manner was then used to inoculate 10 μl of prepared earlier liquid *Lactobacillus* strain cultures using the reduction method, which were then incubated under standard anaerobic conditions for 48 hours. When incubation was completed the strain colonies resistant to given concentration of bile salts turned to light yellow as well as their growth medium turned from violet to yellow color. The growth intensity of the tested strains and the media yellow coloring were measured by using the semi-quantitative scale from − to +++.

The results are shown in Table 3.

TABLE 3

Resistance of *Lactobacillus* strains on bile salts of the following concentrations: 1, 2, 5, 10, 20 g/l.

| Bile salts concentration | *L. fermentum* 57A | *L. plantarum* 57B | *L. gasseri* 57C | Control *L. rhamnosus* GG |
| --- | --- | --- | --- | --- |
| 1 g/l | +++ | +++ | +++ | +++ |
| 2 g/l | +++ | +++ | + | +++ |
| 5 g/l | +++ | +++ | − | +++ |
| 10 g/l | +++ | +++ | − | +++ |
| 20 g/l | +++ | +++ | − | +++ |

4. The Study of the Adhering Properties of the 57A, 57B, 57C Strains and their Mixture to the Human Intestinal Cell Line CaCo2.

The tissue culture of the CaCo2 line was carried out using the multiple passage method for the 20-day period in order to obtain a monolayer. The medium used was a DMEM medium (Dulbecco Minimal Essential Medium) (Gibco) with an additive of 10% of inactivated fetal bovine serum. Additionally, the medium contained 3 mM/ml of L-glutamine and antibiotics: 100 μg/ml$^{-1}$ streptomycin and 100 U/ml$^{-1}$ penicillin. The cultures were carried out at temperature of 37° C. in the atmosphere of increased humidity containing 10% $CO_2$, where the medium was changed twice a week.

The tested *Lactobacillus* strains (individually and later on in a mixed form) were cultured for 48 h in 5 ml of MRS broth in an incubator, at 37° C., under anaerobic conditions, and then centrifuged as a whole (2,000 rpm for 10 min). The supernatant was then discarded and to the bacteria, which deposited at the bottom of the test tube, fresh MRS broth was added in the volume of 1 ml and density was checked using decimal dilutions giving the final value in c.f.u/ml units. Initial density for the 57A strain was $8 \times 10^7$, for 57B strain was $2.5 \times 10^8$, for 57C was $8 \times 10^7$, and for the mixture it was $2 \times 10^9$.

Next, 100 µl of each of the tested bacterial strain suspensions were taken and added to 900 µl of the DMEM tissue culture medium. The mixtures prepared in this manner were then added to the wells containing cells of the CaCo2 cell line. The cells of the tissue line with the tested strains were incubated at 37° C. in atmosphere enriched with 10% $CO_2$ for 30 minutes. After the incubation the cells were washed twice with PBS to get rid of bacteria that were not attached, and then were fixed with 3.7% formaldehyde at room temperature for 1 hour. After the fixation, the cells were washed again with PBS and stained with crystal violet for 3 minutes. The specimen was viewed microscopically under the magnitude of 1000×. The *Lactobacillus* and *Bifidobacterium* cells were counted in 20 visual areas of the specimen and the average values were obtained from 20 areas. The data interpretation were based on the following legend:

The legend concerning the description of the degree of adherence of the tested bacteria of the *Lactobacillus* genus to the intestinal epithelium-CaCo2.

| Degree of adherence | Number of bacterial cells |
| --- | --- |
| +++ | Greater than 80 |
| ++ | Range 60-80 |
| + | Range 40-60 |
| − | Less than 40 |

TABLE 4

Comparison of adherence results to the CaCo2 tissue by bacteria from the genus *Lactobacillus* 57A, 57B, 57C and a mixture of these strains in the presence of the GG controls.

| Strain | CaCo2 tissue** |
| --- | --- |
| *Lactobacillus fermentum* 57A | ++ |
| *Lactobacillus plantarum* 57B | − |
| *Lactobacillus gasseri* 57C | + |
| Mixture of *Lactobacillus* 57A, 57B, 57C strains | ++ |
| Control-*L. rhamnosus* GG | +++ |

The tested strains *L. fermentum* 57A, *L. plantarum* 57B, *L. gasseri* 57C showed great resistance both for low pH (equal to the pH value present in the gastric juice) as well as for artificial gastric juice containing pepsin—the enzyme which is found in gastric juice.

In case of bile salt resistance the strains *L. fermentum* 57A, *L. plantarum* 57B show similar, high resistance for bile salts, opposite to *L. gasseri* 57C, which loses its viability at bile salt concentration of 2 g/l. By analyzing the above data we can predict that the strains *L. fermentum* 57A, *L. plantarim* 57B, *L. gasseri* 57C without any substantial loss in the population number can survive the unfavorable conditions present in the human stomach. In the case of bile salt influence, the strains *L. fermentum* 57A, *L. plantarum* 57B should also not in a significant way change their populations, whereas only the strain *L. gasseri* 57C, having higher viability for bile salts, can lower its population number by a few logs. The above analysis gives evidence of the possibility of using the strains *L. fermentum* 57A, *L. plantarum* 57B, *L. gasseri* 57C administered orally, for colonization of vagina and anus. The tested strains *L. fermentum* 57A, *L. plantarum* 57B, *L. gasseri* 57C showed a very diversified adherence to the intestinal cell line CaCo2. It seems that only the strain *L. fermentum* 57A has a chance to adhere to the human intestinal epithelium, whereas the other two strains do not show this kind of ability. Based on this data we can predict that density of *Lactobacillus* at the endpoint of the large intestine as compared to the density administered in the form of oral preparation may undergo a minor drop not only because of the nature of gastric juice but also as a result of good adhering properties of the strain *L. fermentum* 57A.

II. VISUALIZATION OF CO-AGGREGATION ABILITY OF THE *LACTOBACILLUS* STRAINS MAKING UP THE COMPOSITION

The isolated *Lactobacillus* strains have a unique ability of mutual co-aggregation thanks to which they can be found in a natural combination (co-aggregate) as a mixture of 2 or 3 strains concentrated together due to the surface interactions. This kind of affinity between naturally selected strains colonizing the same ecological niche leads to cooperation in acquiring receptors at the epithelial surface, antagonistic action against others, mainly against pathogenic components of microflora and for a better utilization of available energy sources. The co-aggregation phenomenon was visualized in an example, where:

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

III. COLONIZATION ABILITY OF ANUS AND VAGINA

The composition of the *Lactobacillus* strains has a unique ability to colonize both the digestive tract as well as vagina, which is a consequence of diversity and cooperation of each of its individual components. It can be seen based on the examination of the ability to colonize the anus and vagina in vivo during the clinical trials—the two components of the composition (*Lactobacillus fermentum* 57A and *Lactobacillus plantarum* 57B) after oral administration are present in higher numbers on the anal epithelial surface, whereas the other (*Lactobacillus gasseri* 57C) is present, in higher numbers, at the vaginal epithelium.

Figure 1:
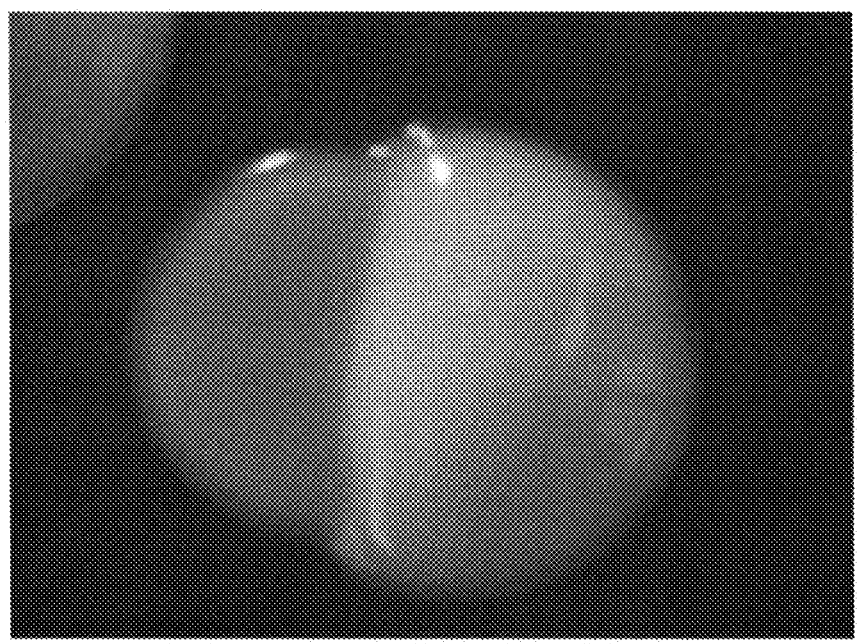
FIG. 1 shows the strain co-aggregation that makes up the composition. Macroscopic picture of a colony showing the presence of two morphologically different components of a single colony (on the left-*L. fermentum*, on the right-*L. plantarum*.).
Figure 2:
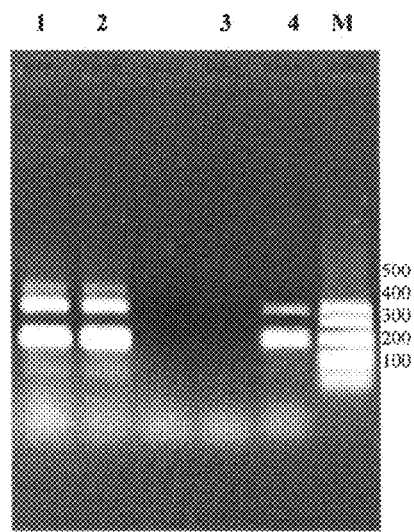
FIG. 2 represents the image of electrophoretically separated bands after the PCR reaction (DNA isolated from a co-aggregate), where a specific starter was used for the genus *L. plantarum*, confirming the presence of *L. plantarum* 57B in the co-aggregate shown in FIG. 1.
Figure 3:
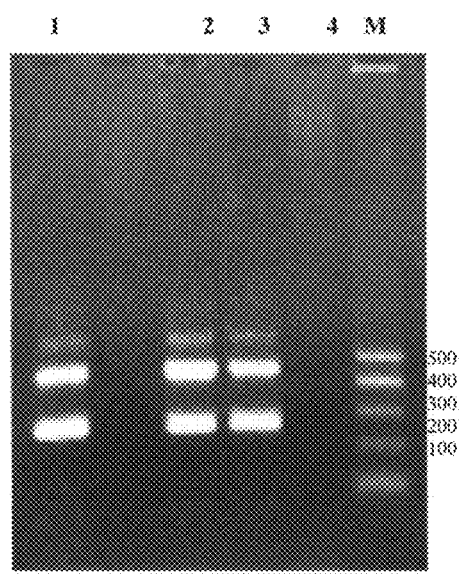
FIG. 3 represents the image of electrophoretically separated bands after the PCR reaction (DNA isolated from a co-aggregate), where a specific starter was used for the genus *L. fermentum*, confirming the presence of the strain *L. fermentum* 57A in the co-aggregate shown in FIG. 1.
Figure 4:
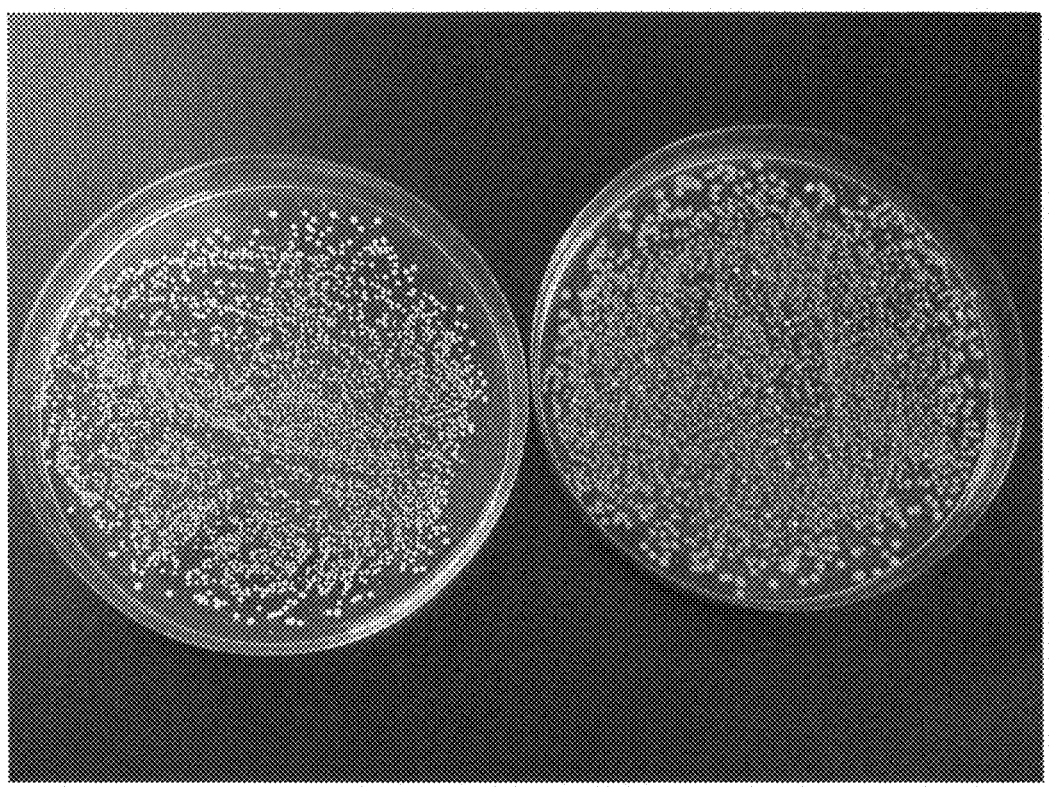
FIG. 4 represents a macroscopic image showing morphologically diversified colonies representing *Lactobacillus* populations colonizing the anal epithelium (left image, domination by *L. plantarum* 57B) and vagina (right image, domination by *L. gasseri* 57C). The sample was taken from a woman who was taking the *Lactobacillus* strain composition for 21 days.

FIG. 4 represents a macroscopic image showing morphologically diversified colonies representing *Lactobacillus* populations colonizing the anal epithelium (left image, domination by *L. plantarum* 57B) and vagina (right image, domination by *L. gasseri* 57C). The sample was taken from a woman who was taking the *Lactobacillus* strain composition for 21 days. The diversified affinity of the *Lactobacillus* strains can be observed in both places in the form of differences in the individual colony numbers.

TABLE 5

An exemplary distribution of the number of *Lactobacillus* strains in vaginal and anal smears of a female patient who used the composition based on the invention.

|  | Colony number-vagina | Colony number-anus |
|---|---|---|
| *Lactobacillus gasseri* 57C | $1 \times 10^8$ | $1 \times 10^3$ |
| *Lactobacillus plantarum* 57B | $3 \times 10^4$ | $1 \times 10^5$ |

WORKING EXAMPLE I

Clinical Trial of the Patients

The clinical trial was carried out for a group of 18 healthy women without any clinical symptoms of genital tract infections, however, with recurrent vaginal infections. The tests showed that oral administration of the *Lactobacillus* strain composition in accordance to the invention resulted in:
1. decrease in the vaginal pH by 0.4
2. decrease in the Nugent's scale indicator by 2 units,
3. increase in the number of *Lactobacillus* strains at the vaginal epithelium by 2 logarithms (log c.f.u/ml).

TABLE 6

Effect of administering the *Lactobacillus* strain composition on the vaginal pH.

| Patient number | Visit I | Visit III-10 | Visit IV-20 | Visit V-31 | Visit VI-50 | Visit VII-62 | Visit VIII-70 |
|---|---|---|---|---|---|---|---|
| 1 | 7 | 5.5 | 5.2 | 5.5 | 5.5 | 5.2 | 5.2 | — |
| 2 | 9 | 4.9 | 4.9 | 4.9 | 5.5 | 4.9 | 4.9 | 4.6 |
| 3 | 27 | 4.9 | 4.6 | 4.4 | 4.2 | 4.4 | 4.6 | 4.6 |
| 4 | 29 | 5.5 | 4.6 | 4.6 | 4.2 | 4.2 | — | — |
| 5 | 5 | 4.6 | 4.6 | 4.9 | 4.9 | 4.6 | 4.6 | 4.2 |
| 6 | 6 | 4.6 | 4.6 | 5.2 | 5.5 | 5.2 | 4.6 | 4.4 |
| 7 | 1 | 5.5 | 5.2 | 5.5 | 4.9 | 4.9 | 4.6 | 5.5 |
| 8 | 25 | 4.0 | 4.2 | 4.4 | 4.0 | 4.2 | 4.0 | 5.2 |
| 9 | 10 | 4.9 | 5.2 | 4.6 | 4.6 | 4.6 | 4.9 | 4.4 |
| 10 | 8 | 5.2 | 5.5 | 4.9 | 4.9 | 4.6 | 4.4 | 4.4 |
| 11 | 11 | 4.4 | 4.9 | 4.0 | 4.2 | 4.2 | 4.2 | 4.4 |
| 12 | 16 | 4.4 | 4.9 | 4.6 | 4.6 | 4.4 | 4.2 | 4.6 |
| 13 | 13 | 4.9 | 5.5 | 4.9 | 4.9 | 4.9 | 4.2 | 4.4 |
| 14 | 12 | 4.6 | 4.6 | 4.9 | 4.9 | 4.6 | 4.6 | 4.6 |
| 15 | 19 | 5.5 | 5.5 | 5.2 | 5.5 | 4.9 | 4.9 | 4.9 |
| 16 | 14 | 5.5 | 4.9 | 4.9 | 4.9 | 4.9 | 4.6 | 4.4 |
| 17 | 21 | 4.9 | 4.6 | 4.6 | 4.9 | 4.9 | 4.4 | — |
| 18 | 23 | 5.5 | 5.5 | 4.4 | 4.9 | 4.4 | 4.6 | 4.6 |
| Average pH |  | 5.0 | 4.9 | 4.8 | 4.8 | 4.6 | 4.6 | 4.6 |

Legend:
— no visit

TABLE 7

Effect of administering the composition of *Lactobacillus* strains on the indicator value of the Nugent's scale. (0-3 normal flora, 4-6 questionable result, 7-10 bacterial vaginosis).

| Patient number | Visit I | Visit III-10 | Visit IV-20 | Visit V-31 | Visit VI-50 | Visit VII-62 | Visit VIII-70 |
|---|---|---|---|---|---|---|---|
| 1 | 7 | 5 | 3 | 1 | 0 | 0 | 2 | — |
| 2 | 9 | 6 | 6 | 6 | 3 | 0 | 1 | 1 |
| 3 | 27 | 1 | 0 | 1 | 0 | 0 | 1 | 1 |
| 4 | 29 | 6 | 5 | 4 | 1 | 1 | — | — |
| 5 | 5 | 1 | 1 | 3 | 3 | 1 | 0 | 1 |
| 6 | 6 | 1 | 1 | 2 | 3 | 1 | 0 | 0 |
| 7 | 1 | 4 | 3 | 3 | 4 | 4 | 2 | 1 |
| 8 | 25 | 0 | 0 | 1 | 0 | 0 | 0 | 1 |
| 9 | 10 | 2 | 3 | 0 | 0 | 0 | 0 | 1 |
| 10 | 8 | 4 | 6 | 3 | 3 | 1 | 1 | 1 |
| 11 | 11 | 1 | 1 | 1 | 0 | 0 | 0 | 1 |
| 12 | 16 | 0 | 1 | 1 | 0 | 1 | 1 | 1 |
| 13 | 13 | 3 | 4 | 3 | 1 | 1 | 1 | 1 |
| 14 | 12 | 2 | 3 | 1 | 1 | 1 | 0 | 2 |
| 15 | 19 | 2 | 2 | 2 | 3 | 1 | 1 | 1 |
| 16 | 14 | 1 | 1 | 1 | 1 | 1 | 1 | 1 |
| 17 | 21 | 1 | 0 | 1 | 0 | 1 | 0 | — |
| 18 | 23 | 5 | 3 | 0 | 0 | 0 | 1 | 1 |
| Average Nugent's value |  | 2.50 (3) | 2.39 (2) | 1.8 (2) | 1.28 (1) | 0.76 (1) | 0.69 (1) | 1.1 (1) |

Legend:
— no visit

TABLE 8

Effect of administering the composition of *Lactobacillus* strains on the total number of the *Lactobacillus* strains (given in c.f.u./ml) colonizing the vaginal epithelium.

| Patient number | Visit I c.f.u/ml | Visit III-10 c.f.u/ml | Visit IV-20 c.f.u/ml | Visit V-31 c.f.u/ml | Visit VI-50 c.f.u/ml | Visit VII-62 c.f.u/ml | Visit VIII-70 c.f.u/ml |
|---|---|---|---|---|---|---|---|
| 1. | 7 | $1 \times 10^1$ | $1 \times 10^5$ | $1 \times 10^4$ | $1 \times 10^5$ | $1 \times 10^4$ | $1 \times 10^6$ | — |
| 2 | 9 | $1 \times 10^4$ | $1 \times 10^4$ | $1 \times 10^0$ | $1 \times 10^3$ | $1 \times 10^3$ | $1 \times 10^7$ | $1 \times 10^3$ |
| 3 | 27 | $1 \times 10^3$ | $1 \times 10^5$ | $1 \times 10^8$ | $1 \times 10^5$ | $1 \times 10^5$ | $1 \times 10^5$ | $1 \times 10^3$ |
| 4 | 29 | $1 \times 10^3$ | $1 \times 10^4$ | $1 \times 10^6$ | $1 \times 10^5$ | $1 \times 10^4$ | $1 \times 10^5$ | $1 \times 10^3$ |
| 5 | 5 | $1 \times 10^0$ | $1 \times 10^0$ | $1 \times 10^3$ | $1 \times 10^5$ | $1 \times 10^0$ | $1 \times 10^3$ | $1 \times 10^0$ |
| 6 | 6 | $1 \times 10^2$ | $1 \times 10^5$ | $1 \times 10^5$ | $1 \times 10^5$ | $1 \times 10^5$ | $1 \times 10^7$ | $1 \times 10^3$ |
| 7 | 1 | $1 \times 10^3$ | $1 \times 10^0$ | $1 \times 10^0$ | $1 \times 10^0$ | $1 \times 10^0$ | $1 \times 10^4$ | $1 \times 10^4$ |

TABLE 8-continued

Effect of administering the composition of *Lactobacillus* strains on the total number of the *Lactobacillus* strains (given in c.f.u./ml) colonizing the vaginal epithelium.

| Patient number | Visit I c.f.u/ml | Visit III-10 c.f.u/ml | Visit IV-20 c.f.u/ml | Visit V-31 c.f.u/ml | Visit VI-50 c.f.u/ml | Visit VII-62 c.f.u/ml | Visit VIII-70 c.f.u/ml |
|---|---|---|---|---|---|---|---|
| 8 | 25 | $1 \times 10^7$ | $1 \times 10^7$ | $1 \times 10^6$ | $1 \times 10^7$ | $1 \times 10^7$ | $1 \times 10^7$ | $1 \times 10^6$ |
| 9 | 10 | $1 \times 10^5$ | $1 \times 10^4$ | $1 \times 10^7$ | $1 \times 10^7$ | $1 \times 10^6$ | $1 \times 10^5$ | $1 \times 10^5$ |
| 10 | 8 | $1 \times 10^1$ | $1 \times 10^0$ | $1 \times 10^4$ | $1 \times 10^6$ | $1 \times 10^3$ | $1 \times 10^3$ | $1 \times 10^3$ |
| 11 | 11 | $1 \times 10^4$ | $1 \times 10^5$ | $1 \times 10^6$ | $1 \times 10^6$ | $1 \times 10^6$ | $1 \times 10^5$ | $1 \times 10^4$ |
| 12 | 16 | $1 \times 10^4$ | $1 \times 10^5$ | $1 \times 10^4$ | $1 \times 10^3$ | $1 \times 10^3$ | $1 \times 10^4$ | $1 \times 10^5$ |
| 13 | 13 | $1 \times 10^4$ | $1 \times 10^4$ | $1 \times 10^6$ | $1 \times 10^5$ | $1 \times 10^7$ | $1 \times 10^6$ | $1 \times 10^7$ |
| 14 | 12 | $1 \times 10^5$ | $1 \times 10^4$ | $1 \times 10^5$ | $1 \times 10^5$ | $1 \times 10^6$ | $1 \times 10^6$ | $1 \times 10^5$ |
| 15 | 19 | $1 \times 10^3$ | $1 \times 10^5$ | $1 \times 10^6$ | $1 \times 10^5$ | $1 \times 10^4$ | $1 \times 10^5$ | $1 \times 10^5$ |
| 16 | 14 | $1 \times 10^0$ | $1 \times 10^0$ | $1 \times 10^7$ | $1 \times 10^0$ | $1 \times 10^0$ | $1 \times 10^5$ | $1 \times 10^3$ |
| 17 | 21 | $1 \times 10^5$ | $1 \times 10^8$ | $1 \times 10^6$ | $1 \times 10^7$ | $1 \times 10^3$ | $1 \times 10^7$ | — |
| 18 | 23 | $1 \times 10^0$ | $1 \times 10^6$ | $1 \times 10^5$ | $1 \times 10^6$ | $1 \times 10^7$ | $1 \times 10^5$ | $1 \times 10^6$ |
| Average total number of *Lactobacillus* | | $1 \times 10^3$ | $1 \times 10^4$ | $1 \times 10^5$ | $1 \times 10^5$ | $1 \times 10^4$ | $1 \times 10^5$ | $1 \times 10^4$ |

Legend:
— no visit

WORKING EXAMPLE II

Pharmaceutical Preparation

One capsule of the pharmaceutical preparation contains:
active substance—$10^9$ of lyophilized *Lactobacillus* strains in the following proportions: 50% *Lactobacillus gasseri* 57C, 25% *Lactobacillus fermentum* 57A, 25% *Lactobacillis plantarum* 57B,
additional substances: lactose, mannitol, nitrogen glutamine, magnesium stearate.

The preparation is administered orally, 1-2 capsules a day with water.

The pharmaceutical preparation is used as a supplement to restore and/or supplement the natural bacterial flora of the urogenital tract as well as to help maintain the right vaginal pH.

The invention claimed is:

1. A method of colonizing a vagina and anus with bacteria comprising administering orally a composition in the form of a capsule containing lyophilized strains of *Lactobacillus fermentum* 57A, *Lactobacillus plantarum* 57B and *Lactobacillus gasseri* 57C to humans;
   allowing the *Lactobacillus fermentum* 57A, *Lactobacillus plantarum* 57B and *Lactobacillus gasseri* 57C to pass through the gastrointestinal tract, and to cross over into the vagina and anus; and
   colonizing the vagina and anus with the *Lactobacillus fermentum* 57A, *Lactobacillus plantarum* 57B and *Lactobacillus gasseri* 57C.

2. The method according to claim 1 wherein upon the colonization of the vagina and the anus, the bacteria *Lactobacillus fermentum* 57A, *Lactobacillus plantarum* 57B and *Lactobacillus gasseri* 57C have a strong affinity to the epithelia of the vagina and anus.

3. A method for preparing the composition of claim 1 further comprising:
   the step of lyophilizing bacterial strains of *Lactobacillus fermentum* 57A, *Lactobacillus plantarum* 57B and *Lactobacillus gasseri* 57C and;
   adding a pharmaceutically acceptable carrier to the lyophilized strains; and
   encapsulating the lyophilized bacterial strains and the carrier to form a capsule containing the composition.

4. The method according to claim 1 further comprising restoring the natural flora of the vagina and anus.

* * * * *